(12) United States Patent
Eckerdal

(10) Patent No.: US 8,442,652 B2
(45) Date of Patent: May 14, 2013

(54) MEDICAL IMPLANTABLE LEAD AND METHOD FOR CONNECTING A MEDICAL IMPLANTABLE LEAD TO AN ORGAN

(75) Inventor: Johan Eckerdal, Knivsta (SE)

(73) Assignee: St. Jude Medical AB, Jarfalla (SE)

( * ) Notice: Subject to any disclaimer, the term of this patent is extended or adjusted under 35 U.S.C. 154(b) by 450 days.

(21) Appl. No.: 12/937,338

(22) PCT Filed: Apr. 11, 2008

(86) PCT No.: PCT/SE2008/000268
§ 371 (c)(1),
(2), (4) Date: Oct. 11, 2010

(87) PCT Pub. No.: WO2009/126070
PCT Pub. Date: Oct. 15, 2009

(65) Prior Publication Data
US 2011/0034982 A1    Feb. 10, 2011

(51) Int. Cl.
*A61N 1/05* (2006.01)
(52) U.S. Cl.
USPC .......................................... 607/116; 607/131
(58) Field of Classification Search ................... 607/116, 607/131
See application file for complete search history.

(56) References Cited

U.S. PATENT DOCUMENTS

| | | | |
|---|---|---|---|
| 4,649,938 A | 3/1987 | McArthur | |
| 4,819,661 A | 4/1989 | Heil, Jr. et al. | |
| 4,913,164 A | 4/1990 | Greene et al. | |
| 5,300,108 A | 4/1994 | Rebell et al. | |
| 5,837,007 A | 11/1998 | Altman et al. | |
| 6,070,653 A | 6/2000 | Wingbro | |
| 6,463,334 B1 | 10/2002 | Flynn et al. | |
| 6,501,990 B1 | 12/2002 | Sundberg et al. | |
| 2003/0093104 A1 | 5/2003 | Bonner et al. | |

*Primary Examiner* — Christopher D Koharski
*Assistant Examiner* — Jeremiah Kimball

(57) ABSTRACT

In a medical implantable lead of the type adapted to be implanted into a human or animal body for monitoring and/or controlling of an organ inside the body and a method for connecting such a lead to an organ in the human or animal body. The lead has a fixation arrangement at a distal end, and the fixation arrangement is adapted to penetrate into the tissue of the organ to fixate the lead to the organ. An electrode member is provided to receive and/or transmit electrical signals from or to the organ. The electrode member is resiliently pre-strained toward the distal end of the lead and is provided with an electrode surface such that the electrode surface will resiliently abut toward the outer surface of the organ when the fixation arrangement is fixed to the tissue.

10 Claims, 6 Drawing Sheets

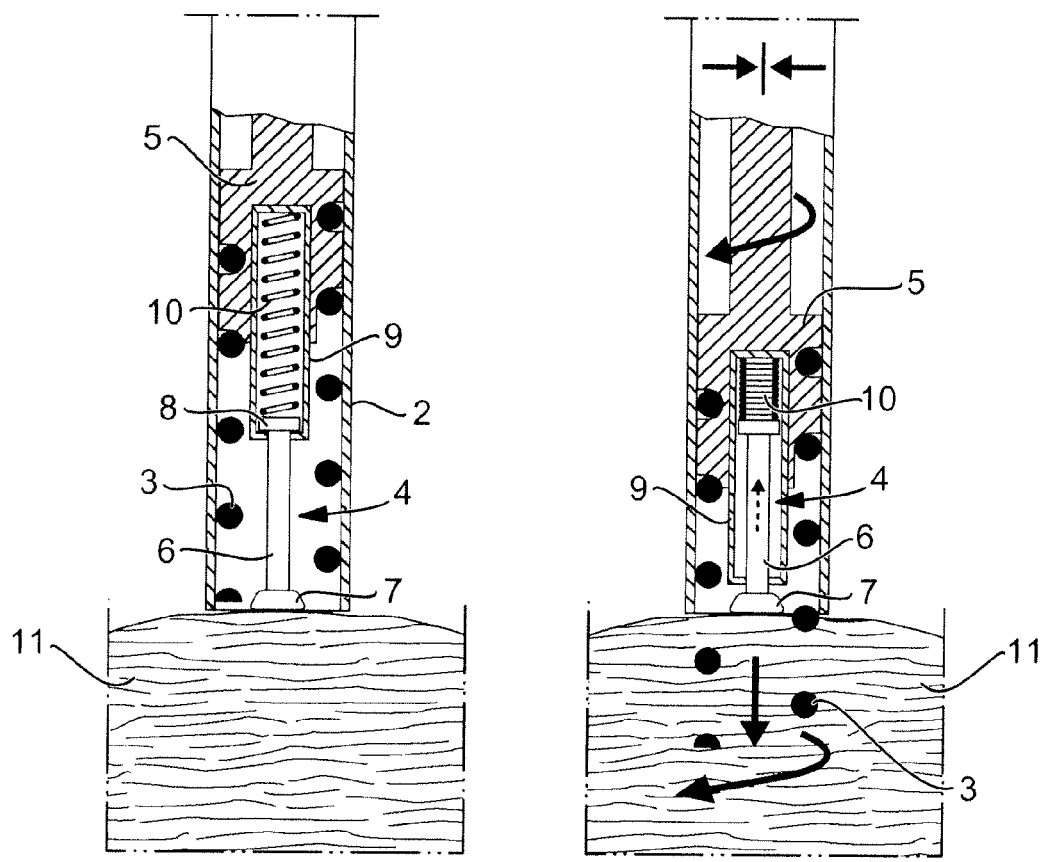

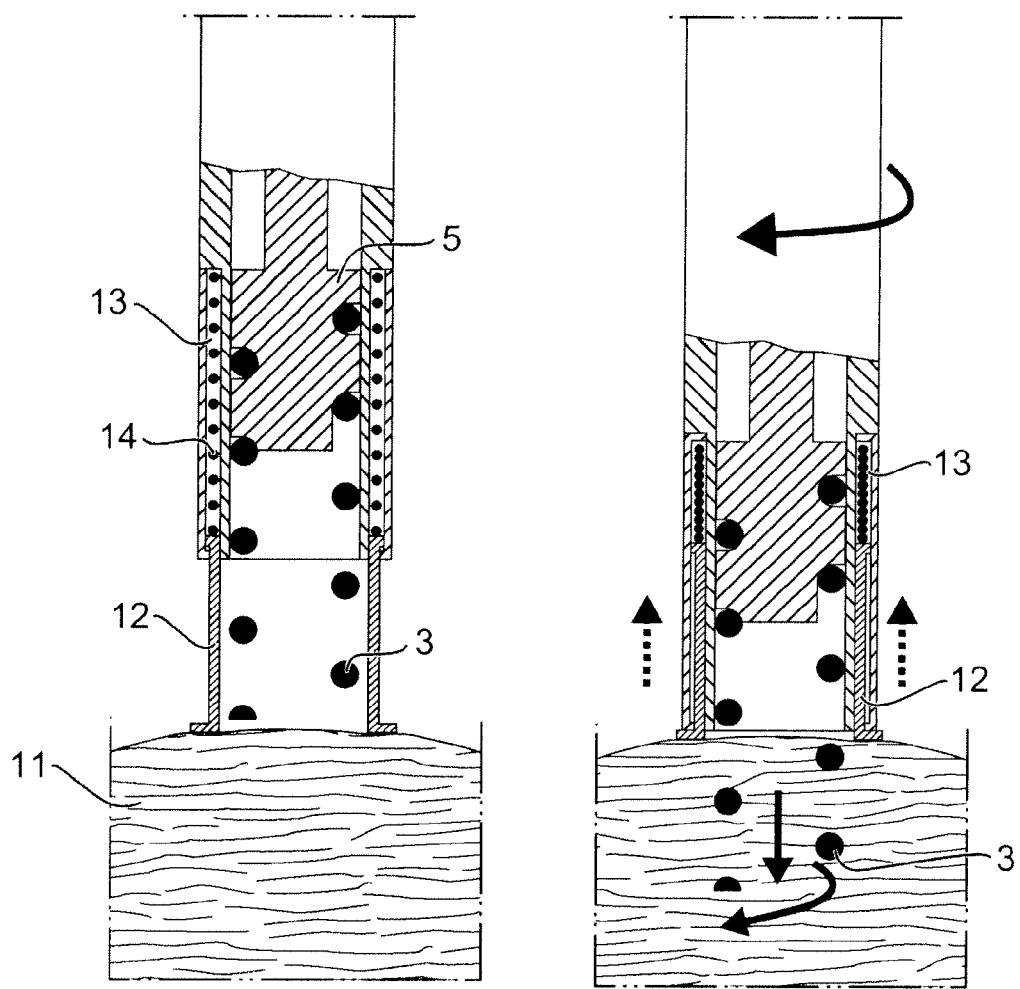

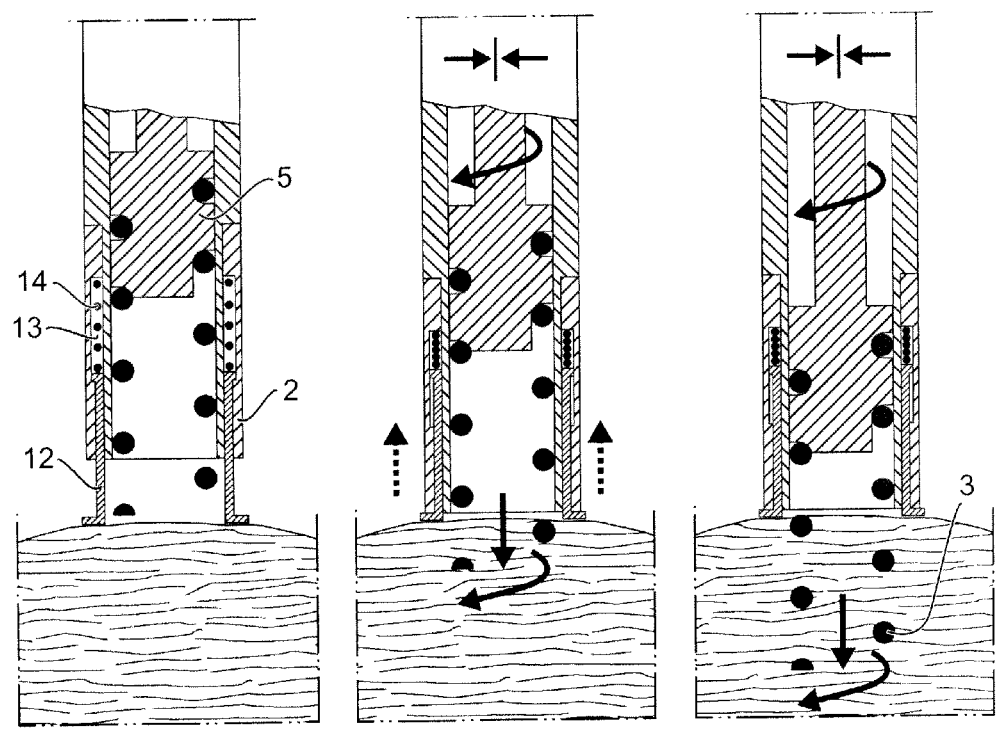

MEDICAL IMPLANTABLE LEAD AND METHOD FOR CONNECTING A MEDICAL IMPLANTABLE LEAD TO AN ORGAN

BACKGROUND OF THE INVENTION

1. Field of the Invention

The invention relates to a medical implantable lead of the type adapted to be implanted into a human or animal body for monitoring and/or controlling of an organ inside the body, and having a fixation means in a distal end, adapted to penetrate into the tissue of the organ to fixate the lead to the organ, and an electrode member to receive and/or transmit electrical signals from or to the organ.

The invention also relates to a method for connecting a medical implantable lead to an organ inside a human or animal body for monitoring and/or controlling the organ by receiving and/or transmitting electrical signals from or to the organ.

2. Description of the Prior Art

It is common knowledge to attach a distal end of a medical implantable lead to an organ inside a human or animal body, in order to monitor and/or control the organ by means of electrical signals. One example of such an application is connection of a pacemaker and/or a defibrillator to a heart but also other applications and other organs could be conceivable. Accordingly, everywhere in the following description and claims where reference is made to a heart, it is to be understood that it shall also apply, where relevant, also to other organs.

Two main methods for connecting the lead to the organ can be distinguished. For so-called passive fixation, the tip of the lead is provided with tines, fins or the like that are adapted to engage in the trabecular network inside the heart. After a few days the lead will be further anchored to the heart by being overgrown by tissue. The other connecting method is a so called active fixation, by which the tip of the lead is provided with a sharp fixation means, such as a rotatable helix or a needle provided with barbs, which is adapted to penetrate into the heart wall and engage thereto. An active fixation lead has some advantages over a passive fixation lead in that the fixation will be more distinct and secure, at least during the first critical days after implantation, and allows as a rule attachment in any arbitrary desired position.

Also the electrode in the distal end of the lead can be provided in essentially two main ways. One possibility is a contact electrode, by which the electrode has an electrode surface which abuts the surface of the tissue. Another is a penetrating electrode, by which the electrode is penetrated into and located in the tissue.

A passive fixation lead is always combined with a contact electrode. An active fixation lead has its electrode normally integrated with the active fixation means such that the helix or the needle also functions as the electrode. However, it is also known active fixation leads, where the fixation means, e.g. a helix, is electrically insulated and instead the lead is provided with a separate contact electrode, which abuts against the surface of the tissue.

When implanting an electronic device in a body, it is important to ensure a long operational life in order to avoid frequent replacement of the device. Normally, it is the battery life in the electronic device that is the limiting factor. Accordingly, it is important to keep the energy consumption of the device down to attain a long operational life. It is primarily two parameters which are essential for a low energy consumption. That is the impedance of the electrode and the capture threshold of the signal transfer between the electrode and tissue. With a high impedance in the electrode, the current consumption can be restricted and with a low capture threshold, the required voltage for transferring signals to the tissue will be low.

A high impedance is normally achieved by reducing the electrode area. In the case of a helix electrode, which is the most common example of a lead having an active fixation, a high impedance can be achieved by partly providing the helix with an electrically insulating coating. Low capture threshold can be achieved by enabling good contact of the electrode with excitable tissue. When using an active fixation lead with the electrode integrated in the fixation element, e.g. a helix which is screwed into the tissue, a good electrical contact is normally attained initially. However, since the electrode is causing a trauma as it penetrates into the tissue, the electrical contact will deteriorate within a few days due to the inflammatory process and the subsequent fibrous capsule formation.

As mentioned it is known to use active fixation leads that have a separate contact electrode, e.g. by combining an insulated helix with an electrode surface provided on the tip of the lead, which abuts against the surface of the tissue when the helix is screwed into the tissue. However, in this case it is not ensured that the electrical contact will be good in case the helix is not inserted deep enough into the tissue or the helix is partly dislodged.

SUMMARY OF THE INVENTION

An object of the present invention is to provide an improved medical implantable lead, which eliminates disadvantages of prior art leads. More precisely, it is an object to provide a medical implantable lead by which it is possible to achieve a distinct and secure attachment to an organ at the same time as the electrical connection to the organ can be made with a high impedance and a low capture threshold.

The invention also relates to a method for connecting a medical implantable lead to an organ inside a human or animal body, having essentially the same object as above. At least this object is achieved by a method according to claim 10.

The basis of the invention is the insight that the above object may be achieved by combining an active fixation with a separate contact electrode, which is resiliently arranged in the distal end of the lead and biased with its electrode surface in the longitudinal direction of the lead toward the distal end. In this way a secure and reliable active fixation can be combined with a low capture threshold surface contact electrode, which is biased toward the tissue such that a good contact can be achieved regardless of how the active fixation is carried out, i.e. regard less of the degree of fixation that is achieved by means of the active fixation means. Since the electrode is not penetrated into the tissue, there will be no fibrous capsule formation or the like around the electrode which can increase the capture threshold.

Within this general idea the invention may be modified in many different ways. In all of the embodiments, which are described and illustrated hereinafter, the active fixation means has the form of a helix, which is rotatable and adapted to be screwed into the tissue for fixation. One advantage with a helix is that it normally gives a reliable fixation and yet easily can be detached from the tissue, if desired, by reversed rotating of the helix, without risk for causing additional trauma in the tissue. However, also other kinds of active fixation means could be conceivable, especially if it is of a type which can be detached without causing trauma.

In several of the following embodiments, the electrode has the form of a spring loaded pin, which is centrally positioned within the helix, such that when screwing the helix into the tissue, an outer electrode surface of the pin will abut and make contact with the tissue surface. It is also possible, as is disclosed in one embodiment, to form the electrode itself as a spring, e.g. a helical spring, which in an outer end is provided with an electrode surface. In yet other embodiments, the electrode is formed as a sleeve, which surrounds the helix, is biased from a so called header in a distal end of the lead and connects with a circular electrode surface to the tissue when the helix is screwed into the tissue. One advantage with the latter embodiment in relation to the others is that the electrode surface will be positioned outside the helix, i.e. outside of the area which is exposed to trauma which can increase the possibilities of finding a low capture threshold contact with electrically excitable tissue.

In all of the following embodiments, the electrode member is spring loaded by a resilient means in form of a helical spring. It is to be understood, however, that also other kinds of resilient means could be used. For example a leaf spring or even a resilient material as long as the electrical conduction to the electrode can be arranged.

As a rule it is preferred that the active fixation means is electrically non-conducting, such that only the electrode is electrically conducting. However, it can not be excluded that in certain circumstances it could be an advantage if also the fixation means could be electrical conducting. For example to use the fixation means as an auxiliary electrode in case the regular electrode should fail or to arrange the lead as a bipolar lead by which the electrode and the fixation means has different electrical potential.

BRIEF DESCRIPTION OF THE DRAWINGS

FIG. 2 is a schematic longitudinal section, in enlarged scale, through the distal end of the lead according to a first embodiment of the invention in an initial position.

FIG. 3 is a schematic longitudinal section of the lead according to FIG. 2 in a fixated state.

FIG. 6 is a schematic longitudinal section of a lead according to a third embodiment in an initial position.

FIG. 7 is a schematic longitudinal section of the lead according to FIG. 6 in a fixated state.

FIG. 8 is a schematic longitudinal section of a lead according to a fourth embodiment in an initial position.

FIG. 9 is a schematic longitudinal section of the lead according to FIG. 8 in a partly fixated state.

FIG. 10 is a schematic longitudinal section of the lead according to FIGS. 8 and 9 in a completely fixated state.

DESCRIPTION OF THE PREFERRED EMBODIMENTS

Figure 1:
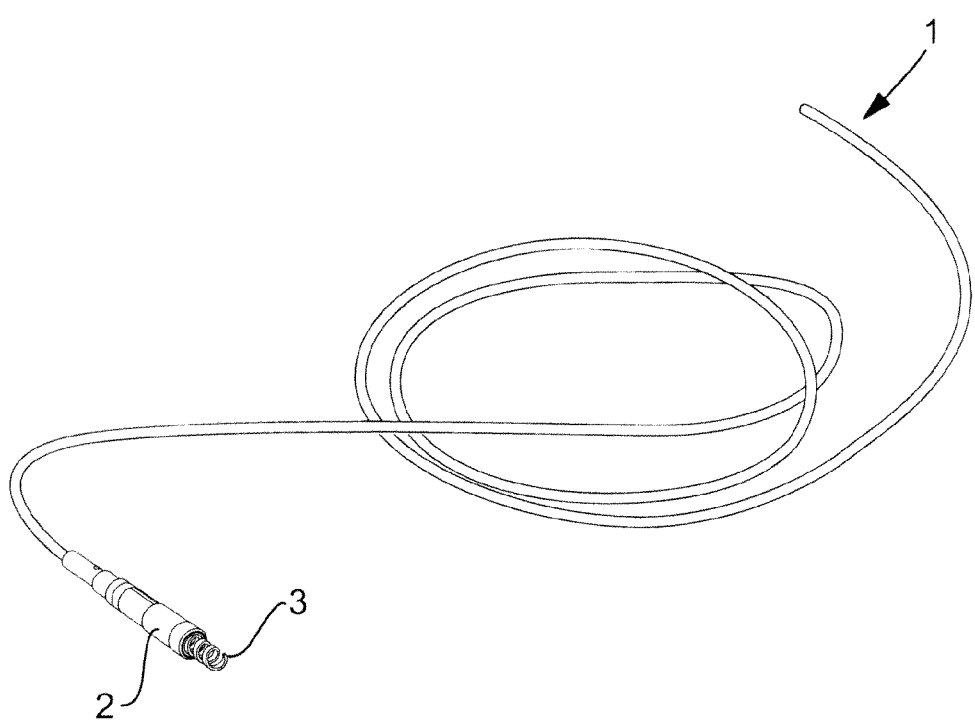
FIG. 1 is a perspective view of an electrical lead adapted to connect a pacemaker or defibrillator with a heart.

FIG. 1 illustrates an example of an electrical lead for connecting a pacemaker or a defibrillator to a heart. The lead comprises a proximal end 1, which is adapted to be connected to a not shown pacemaker or defibrillator, and a distal end adapted to be attached to the tissue of a heart. The distal end comprises a so called header 2, which is formed as a sleeve and accommodates a helix 3, which is adapted to be attached to the heart by being screwed into the tissue of the heart.

Next, reference is made to FIGS. 2 and 3 for describing a first embodiment of the invention. Inside the header 2 the lead is provided with a helix 3 and an electrode pin 4. The helix 3 as well as the electrode pin 4 is mounted in a coupling 5 such that they project forward towards the distal end of the lead from the coupling. More precisely, the helix 3 is mounted on the outside of the coupling, whereas the electrode pin 4 is mounted in the central of the coupling and positioned within the helix. Moreover, the electrode pin is formed with an elongated shaft 6, a head 7 having an electrode surface in a distal end and a stop member 8 in a proximal end. The stop member 8 is positioned inside a spring housing 9 such that the elongated shaft 6 projects displaceable from a forward opening in the spring housing. A spring 10 inside the spring housing actuates the electrode pin 4 to be displaced in the direction forward towards the distal end of the lead by acting between the proximal end of the spring housing and the stop member 8. In an initial state, as is illustrated in FIG. 2, the helix 3 as well as the electrode pin 4 are entirely accommodated inside the header 2 and the electrode pin 4 is displaced as far as possible in the direction forward such that both the most distal end of the helix as well as the most distal end of the electrode pin, i.e. the electrode surface, are positioned essentially flush with the distal end of the header 2. The coupling 5 is rotatable and displaceable in the longitudinal direction of the lead, when rotated from the proximal end by means of a not shown rotary means inside the lead. Accordingly, when the lead, in its initial state, is positioned with its distal end abutting against the tissue of a heart 11, as illustrated in FIG. 2, and the coupling 5 is subsequently rotated, the helix 3 will be screw rotated and penetrate into the tissue, as illustrated in FIG. 3. The electrode surface at the distal end of the head 7 of the electrode pin 4, will however abut against the tissue and, as the helix 5 is penetrated into the tissue, the shaft 6 will be displaced inwards into the spring housing 9 and the spring 10 will be compressed, such that the electrode surface abuts the tissue by a force determined by the spring force. The helix 3 will cause some trauma when penetrated into the tissue but the electrode surface of the electrode pin 4 will abut the tissue in a region within the helix where no trauma is caused. Accordingly, there is a low risk that the electrical contact between the electrode pin and the tissue will be interfered by fibrous capsule formation and scar formation.

Figure 4:
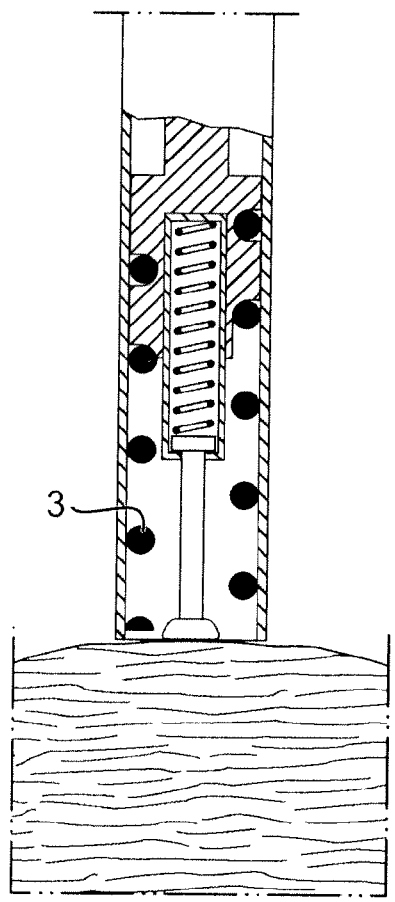
FIG. 4 is a schematic longitudinal section of a lead according to a second embodiment in an initial position.
Figure 5:
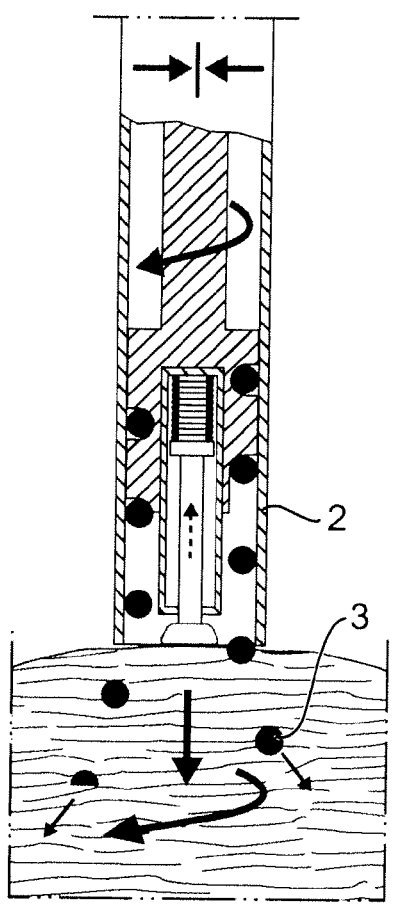
FIG. 5 is a schematic longitudinal section of the lead according to FIG. 4 in a fixated state.

A second embodiment according to FIGS. 4 and 5 is similar to the first embodiment in FIGS. 2 and 3, except that here the helix 3 is of an expandable type, which will expand outwards and adopt a larger diameter as soon as it leaves the inner bore of the header 2, as is illustrated in FIG. 5. In this way the region within the helix being free from trauma and scar formation will increase which may lower the capture threshold.

In a third embodiment according to FIGS. 6 and 7, the electrode is not in form of a pin positioned within the helix, as in the first and second embodiments. Instead, the electrode has the form of an electrode sleeve 12, which is displaceable arranged in a slot 13 in the distal end of the header 2. The electrode sleeve is actuated by a spring 14 to adopt a maximum projecting position from the header 2. The distal circular end surface of the electrode sleeve 12 functions as an electrode surface against the tissue 11. As in the previous embodiments, the helix 3 is mounted in a coupling 5. However, here the coupling is not rotatable, nor displaceable. Instead, when attaching the lead to the tissue, the entire lead is rotated at the same time as the lead is pressed towards the tissue, when in the initial position as illustrated in FIG. 6. When the helix penetrates into and engages the tissue, the helix is screwed in at the same time as the electrode sleeve 12 is displaced into the slot 13 against the action from the spring 14. In operation, as illustrated in FIG. 7, the electrode surface of the electrode sleeve 12 will abut the tissue, by a spring force, in the unaffected area around the helix.

A fourth embodiment according to FIGS. 8-10 is similar to the third embodiment according to FIGS. 6 and 7, in that it is provided with an electrode sleeve 12 being displaceable against the action of a spring 14 in a slot 13 in the header 2. However, here this feature is combined with a rotatable and displaceable coupling 5. When attaching the lead to the tissue, this is made possible by a combination of displacing of the electrode sleeve 12, as illustrated in FIG. 9, and rotation and displacing of the coupling 5 and the helix 3 towards the distal end, as illustrated in FIG. 10. One advantage with this embodiment is that the electrode sleeve can be made shorter and with a shorter length of stroke.

Figure 11:
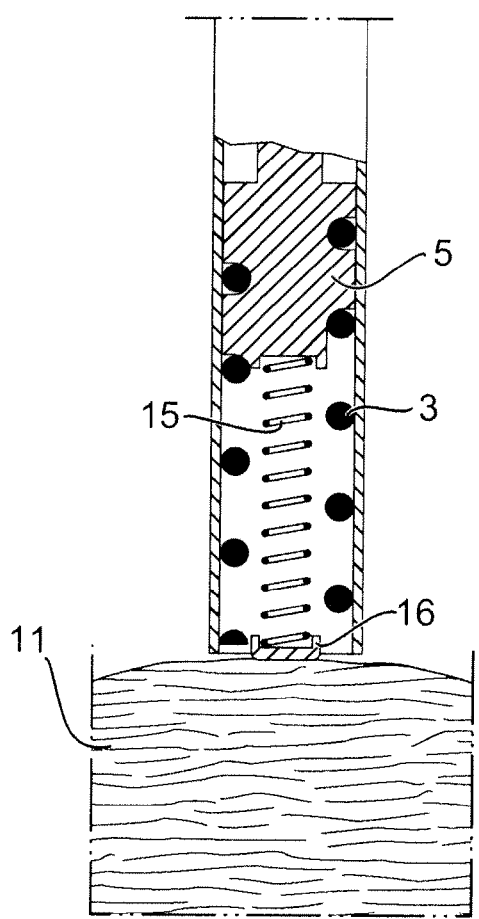
FIG. 11 is a schematic longitudinal section of a lead according to a fifth embodiment in an initial position.
Figure 12:
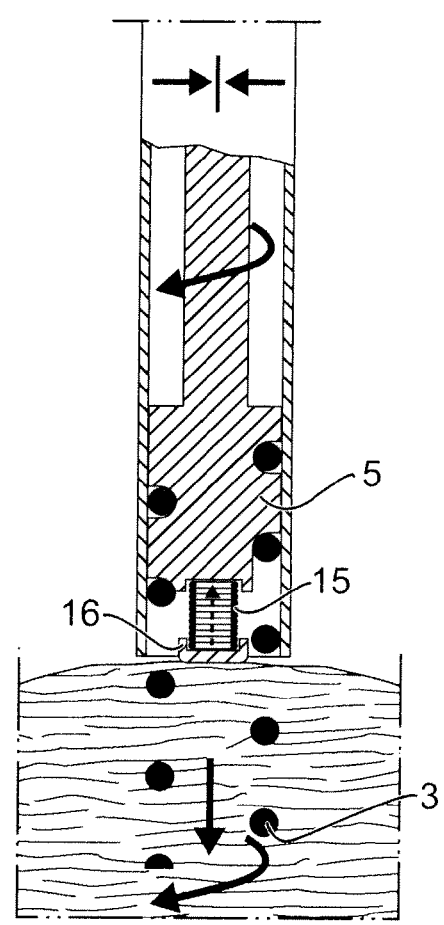
FIG. 12 is a schematic longitudinal section of the lead according to FIG. 10 in a fixated state.

A fifth embodiment is illustrated in FIGS. 11 and 12. In this embodiment the electrode itself is formed as a helical spring 15, which is provided with a disc 16 in its distal end for forming of a electrode surface with a sufficient area. The electrode spring 15 is arranged centrally within the helix 3 and the helix as well as the electrode spring is mounted on a rotatable as well as displaceable coupling 5. When connecting the distal end of the lead to the tissue 11, as illustrated in FIG. 12, the coupling is rotated by a not shown rotary means from the proximal end, such that the coupling together with the helix and the electrode spring will be displaced forward towards the distal end of the lead. Accordingly, the helix 3 will penetrate and be screwed into the tissue, whereas the electrode spring 15 will abut with its distal disc 16 against the tissue and be compressed.

Although modifications and changes may be suggested by those skilled in the art, it is the intention of the inventor to embody within the patent warranted heron all changes and modifications as reasonably and properly come within the scope of his contribution to the art.

I claim as my invention:

1. An implantable medical lead comprising:
    a lead body adapted for in vivo implantation in a subject, said lead body comprising a proximal end adapted for connection to an implantable medical device, and a distal end, opposite said proximal end, adapted for in vivo attachment to tissue at a surface of an organ;
    a fixation arrangement at said distal end of said lead body that penetrates into said tissue to fix said distal end at said site;
    an electrode member extending in said lead body from said proximal end to said distal end, said electrode member comprising an electrode surface; and
    said electrode member being resiliently pre-strained toward said distal end of said lead body to resiliently abut said electrode surface toward said outer surface of said organ when said fixation arrangement is fixed to said tissue.

2. The implantable medical lead as claimed in claim 1 wherein said fixation arrangement is a rotatable helix.

3. The implantable medical lead as claimed in claim 2 wherein said helix is configured to expand when penetrating into said tissue of said organ.

4. The implantable medical lead as claimed in claim 1 comprising a helical spring that resiliently pre-strains said electrode member toward said distal end of said lead body.

5. The implantable medical lead as claimed in claim 1 comprising a coupling to which said fixation arrangement and said electrode member are attached, said coupling being rotatable and displaceable in a longitudinal direction of said lead body.

6. The implantable medical lead as claimed in claim 1 wherein said electrode member is an electrode pin.

7. The implantable medical lead as claimed in claim 6 comprising a housing in which said electrode pin is displaceable.

8. The implantable medical lead as claimed in claim 1 wherein said electrode member comprises a sleeve that is displaceable in a longitudinal direction of said lead body, and a spring that resiliently pre-strains said sleeve toward said distal end of said lead body.

9. The implantable medical lead as claimed in claim 1 wherein said electrode member is a spring element.

10. A method for connecting an implantable medical lead in vivo to an organ, comprising:
    actively fixing an electrode member of an implantable medical lead in vivo to an organ using an active fixation arrangement that is movable in a longitudinal direction of the lead;
    resiliently pre-straining said electrode toward a distal end of said lead with a spring member contained in said lead; and
    mounting said distal end of said lead to said organ by penetrating the fixation arrangement into tissue of the organ to abut the electrode against said tissue by moving the electrode in said longitudinal direction against action of said spring.

* * * * *